United States Patent [19]

Grimm

[11] Patent Number: 4,770,270
[45] Date of Patent: Sep. 13, 1988

[54] STETHOSCOPE CHESTPIECE WITH A SOUND CONVEYING INDEXING DETENT

[75] Inventor: Forrest R. Grimm, Golden Valley, Minn.

[73] Assignee: Minnesota Mining and Manufacturing Company, St. Paul, Minn.

[21] Appl. No.: 49,315

[22] Filed: May 13, 1987

[51] Int. Cl.⁴ .......................................... H04R 25/00
[52] U.S. Cl. .................... 181/137; 181/131
[58] Field of Search .............................. 181/131, 137

[56] References Cited

U.S. PATENT DOCUMENTS

| | | | |
|---|---|---|---|
| 3,124,211 | 3/1964 | Cefaly | 181/131 |
| 3,152,659 | 10/1964 | Littmann | 181/137 |
| 3,224,526 | 12/1965 | Weber | 181/137 |
| 3,316,998 | 5/1967 | Krug | 181/137 |
| 4,212,368 | 7/1980 | Allen | 181/131 |
| 4,239,089 | 12/1980 | Nelson | 181/131 |

*Primary Examiner*—B. R. Fuller
*Attorney, Agent, or Firm*—Donald M. Sell; James A. Smith; Dale E. Hulse

[57] ABSTRACT

A stethoscope chestpiece has a body member, a tubular shaft, and an indexing detent. The body has a plurality of microphones each of which has a opening at its apex and a central recess. The tubular shaft is rotably secured within the central recess and has an opening in its wall that aligns selectively with one of the openings from the microphones. The sound conveying detent is mounted transversely within the shaft and aligned with the opening in the shaft wall. The indexing detent has a hollow cylindrical element and spring. The hollow cylindrical element has an open bottom and a seat end having an opening. The seat end is beveled and extends beyond the opening in the shaft wall to engage the body. When the seat end is aligned with a selected one of the openings from the microphones it seats to hold the opening from the microphone in alignment with the opening in the seat end to create a sound passageway into the tubular shaft.

6 Claims, 1 Drawing Sheet

STETHOSCOPE CHESTPIECE WITH A SOUND CONVEYING INDEXING DETENT

FIELD OF THE INVENTION

The present invention relates to a multiple microphone stethoscope chestpiece having a novel and improved sound conveying detent for aligning a tubular shaft in a central recess of the body of the chestpiece with a selected one of the openings from the microphones to the central recess.

BACKGROUND OF THE INVENTION

Two microphone stethoscope chestpiece constructions are well known and generally have a tubular stem or shaft secured in a body and rotatably alignable with a selected one of the microphones (e.g., a conventional bell microphone for low frequency heart sounds or a conventional diaphragm microphone for high frequency lung sounds). Typically the shaft has a spring loaded detent to hold the shaft in alignment with the selected microphone while blocking sound transmission into the stem from the microphone not in use. Manufacture of chestpieces with indexing detents is very expensive because of multiple machining steps to mate the various parts, complex assembly, and extensive testing to assure that no sound leaks into the stem from pathways other than the selected microphone.

U.S. Pat. No. 3,224,526 to Weber describes an indexing detent that has been used for many years with cardiology stethoscopes (having a relatively large stem). The indexing detent is comprised of a coil spring lying transversely of the stem and wholly within the stem and a stop. The assembly of the coil spring and stop aligns with two openings in the wall of the stem. The stop is preferably a ball bearing carefully machined to seat in an opening at the apex of the microphone not in use. Sound enters the stem from the microphone in use through a hole in the microphone at its apex that is aligned with the hole in the stem opposite the stop. When pressure is applied to the stem to rotate it, the ball bearing is biased against the spring inside the stem and rotates within the stem. When proper alignment is reached, the compression on the spring is released and the ball bearing is forced against the opening to the microphone not in use and prevents air leakage. While stethoscopes carefully manufactured according to this design work very well over a long period of time, the manufacturing cost is high. The ball bearing and the openings from each of the microphones must be carefully machined to mate and they must be individually tested for second leaks across the ball bearing-microphone seal. Additionally, any wear on the microphone opening or the ball bearing (e.g., from foreign matter) can create sound leaks.

U.S. Pat. No. 3,152,659 to Littman describes another indexing detent that has performed very well for many years in stethoscopes having smaller stems than cardiology stethoscopes. The body of the chestpieces has two diametrically opposed microphones and a central bore. Each microphone has an opening into the central bore. The openings are aligned across the bore. The bore is machined to have two grooves that are spaced normal to the openings. A U-spring is fit within the end of the stem. The U-spring has enlarged bight sections which resiliently engage the grooves in the bore. The position of the U-spring may be locked with respect to the stem by providing short slits along the end of the stem through which the enlarged bight sections of the U-spring extend. Manufacture of this chestpiece requires very close tolerances to assure that the grooves are normal to the openings from the microphones, that the slits in the stem are normal to the opening in the stem, that the U-spring mates with the grooves without allowing the stem to wobble and with appropriate resiliency to allow detent indexing. While stethoscopes made with this design perform very well, maintenance is required if the U-spring breaks. Eventually the grooves in the bore wear so that the U-spring does not securely hold the hole in the stem in alignment with the selected opening, requiring replacement of the entire chestpiece.

SUMMARY OF THE INVENTION

The construction of the present invention overcomes the problem of sound leaks across the interface between a ball bearing and a hole in the microphone not in use and the expensive manufacture and maintenance costs of the U-spring construction. It is also suitable for use with chestpieces having more than two microphones (e.g., the chestpiece of U.S. Pat. No. 3,124,211 has three microphones). The invention is a chestpiece having a body member, a tubular shaft and an indexing detent. The body member has a plurality of microphones and a cylindrical central recess. Each microphone has an opening at its apex into the central recess. The openings are placed with their centers in a common plane which is normal to the axis of the recess. The tubular shaft is rotatably secured within the central recess and has a single opening in its wall. The opening in the wall is adapted upon rotation to be aligned selectively with any one of the openings in the microphones. The indexing detent is mounted transversely within the shaft and aligned with the opening in the shaft wall. The indexing detent has a hollow cylindrical element and a spring. The hollow cylindrical element is open at both ends to allow sound to pass undampened therethrough and has one end which is beveled to form a seat end. The spring is positioned to resiliently urge cylindrical element out of the tubular shaft. The seat end protrudes out of the opening in the wall of the tubular shaft and engages the body member. Upon rotation of the tubular shaft the seat end rotates into alignment with a selected one of the openings in the microphones and seats to hold the alignment of the microphone opening with the opening in the seat end to create an unrestricted passageway. Upon further rotation of the tubular shaft, the seat end rotates into alignment with another one of the openings from the microphone.

Preferably the tubular shaft is secured against axial movement within the recess and the body has two microphones diametrically arranged about the central recess. In the preferred construction, the seat end is frustroconical and is beveled at an angle between 45° and 60° from a plane normal to the axis of the cylindrical element. The most preferred angle for the bevel of the seat end is 50°. Additionally, the hollow cylindrical element has sufficient height so that it rotates as a unit with the tubular shaft when torque is applied to the shaft and does not tilt in the opening from the shaft and bind.

DETAILED DESCRIPTION

Figure 1:
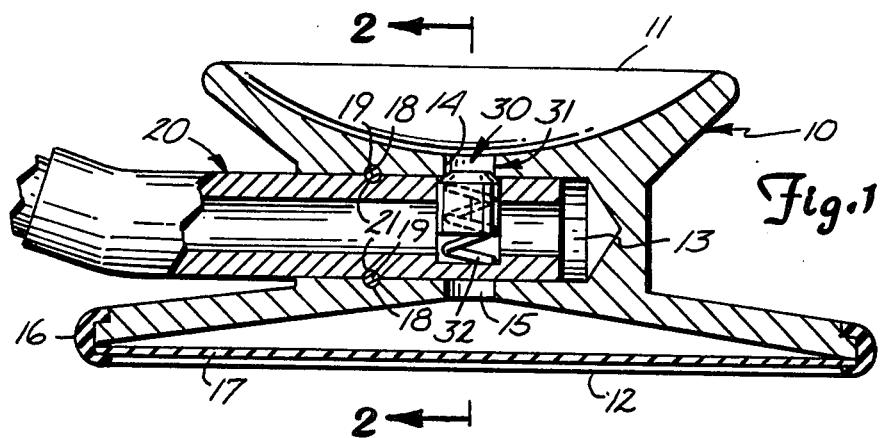
FIG. 1 is a longitudinal sectional view of the chestpiece showing the indexing detent positioned for use for the bell shaped microphone.
Figure 2:
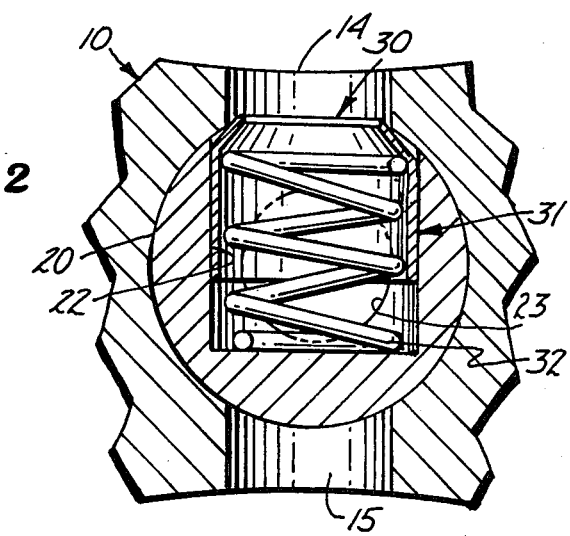
FIG. 2 is an enlarged sectional view taken along line 2—2 of FIG. 1.
Figure 3:
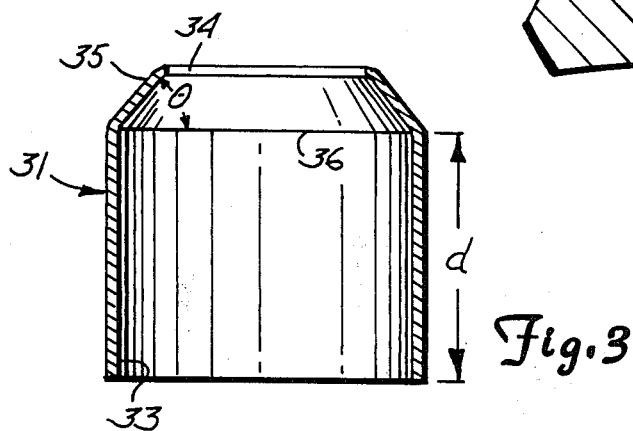
FIG. 3 is a sectional view of the cylindrical hollow element.

The preferred stethoscope chestpiece has a body 10, a tubular shaft 20, and an indexing detent 30. The body 10 is shown with two microphones, a conventional bell type microphone 11 and a conventional diaphragm type microphone 12. The two microphones are diametrically arranged around a cylindrical central recess 13. The bell type microphone 11 has an opening 14 at its apex while the diaphragm type microphone 12 has an opening 15 at its apex. Also, shown are a retaining ring 16 and diaphragm 17 which are well known to those skilled in the art.

The tubular shaft 20 is rotatably secured within the recess 13. The body 10 has a circular groove 18 along the inside wall of recess 13 and the tubular shaft has a corresponding circular groove 21 along its outer surface. Groove 18 and 21 contain lock ring 19 which secures the tubular shaft against axial movement.

The tubular shaft 20 is shown aligned with opening 14 from the bell microphone 11. Rotation of the tubular shaft 20 through 180° would bring opening 22 into alignment with opening 15 in the diaphragm microphone 12.

The indexing detent 30 has a hollow cylindrical element 31 and a spring 32. The hollow cylindrical element 31 has an open bottom 33 and an opening 34 in its seat end 35. The seat end 35 has a beveled contour at an angle Θ from the plane 36 normal to the axis of the hollow cylindrical element 31. Preferably the angle Θ is between 45° and 60°. Most preferably the angle Θ is 50°. The hollow cylindrical element also has a height d which is long enough so that the hollow cylindrical element rotates as a unit with the tubular shaft when torque is applied to the shaft. Those skilled in the art will appreciate that too short a height d may allow the cylindrical element 31 to tilt relative to the opening in the shaft and bind. The length d should also be short enough to leave a space between its open bottom 33 and the bottom of the bore 23 in the shaft when the seat end is seated against one of the openings in the microphone. This space allows sound traveling through the cylindrical element 31 to pass into the tubular shaft and into a tubular binaural (not shown) in the conventional manner.

The spring 32 is shown as a conventional coil spring positioned partially within the hollow cylindrical element 31 and urging it against body 10. The spring may be formed in any convenient manner provided that sound communication exists between the open bottom of the hollow cylindrical element and the tubular shaft.

The foregoing description has been directed to the preferred stethoscope chestpiece. Those skilled in the art will appreciate that many variations are possible without departing from the scope of the claims that follow.

What is claimed is:

1. A stethoscope chestpiece comprising a body member, a tubular shaft and an indexing detent means wherein the body member comprises a plurality of microphones, a cylindrical recess interposed between the microphones, and openings from the apex of each microphone communicating with the recess with each such opening having its center in a common plane normal to the axis of the cylindrical recess;

the tubular shaft is rotatably secured within the cylindrical recess and has a single opening through the wall of the shaft adapted on rotation of the shaft to be aligned selectively with any one of the openings in the microphone; and the indexing detent is mounted transversely within the shaft aligned with the opening in its wall and is comprised of a hollow cylindrical element and a spring, the hollow cylindrical element having a seat end and an opposite end, the seat end being beveled and extending beyond the opening of the wall of the shaft, the seat end and the opposite end each having openings to permit sound to pass undampened therethrough, and the spring being positioned to resiliently urge the seat end against the body member so that upon rotation of the tubular shaft the seat end rotates into alignment with a selected one of the openings from the microphones and seats to hold the opening from the microphone in alignment with the opening in the seat end to create a passageway until further rotation of the tubular shaft causes the seat end to rotate to align with another one of the openings from the microphones.

2. The stethoscope chestpiece of claim 1 further comprising means to secure the tubular shaft against axial movement within the recess.

3. The stethoscope chestpiece of claim 1 wherein the body has two microphones, one being a bell type and the other a diaphragm type.

4. The stethoscope of claim 1 wherein the seat end is a frustroconical section.

5. The stethoscope of claim 4 wherein the angle of the frustroconical section is between 45°–60° from a plane defined by the circumference of the section.

6. The stethoscope of claim 1 wherein the hollow cylindrical element has a height sufficient to cause the cylindrical element to rotate as a unit with the tubular shaft when torque is applied to the tubular shaft.

* * * * *